US011408170B2

(12) United States Patent
Hodsden et al.

(10) Patent No.: US 11,408,170 B2
(45) Date of Patent: Aug. 9, 2022

(54) UNIVERSAL PRE-FABRICATED OPERATING ROOM CEILING SYSTEM

(71) Applicant: Flexible OR Solutions LLC, Dripping Springs, TX (US)

(72) Inventors: Scott Hodsden, Dripping Springs, TX (US); Julie Hodsden, Dripping Springs, TX (US)

(73) Assignee: Flexible OR Solutions LLC, Dripping Springs, TX (US)

( * ) Notice: Subject to any disclaimer, the term of this patent is extended or adjusted under 35 U.S.C. 154(b) by 199 days.

(21) Appl. No.: 16/783,353

(22) Filed: Feb. 6, 2020

(65) Prior Publication Data
US 2020/0248449 A1 Aug. 6, 2020

Related U.S. Application Data

(60) Provisional application No. 62/801,879, filed on Feb. 6, 2019.

(51) Int. Cl.
*E04B 9/00* (2006.01)
*E04B 9/02* (2006.01)
*E04F 17/04* (2006.01)
*F24F 7/007* (2006.01)
*A61G 10/02* (2006.01)
*A61B 90/30* (2016.01)
*E04B 9/18* (2006.01)

(52) U.S. Cl.
CPC .............. *E04B 9/006* (2013.01); *A61B 90/30* (2016.02); *A61G 10/02* (2013.01); *E04B 9/02* (2013.01); *E04B 9/18* (2013.01); *E04F 17/04* (2013.01); *F24F 7/007* (2013.01); *E04B 2009/026* (2013.01)

(58) Field of Classification Search
CPC ...... A61B 90/30; A61G 10/02; A61G 12/004; A61G 2210/70; A61G 2210/90; E04B 9/006; E04B 9/02; E04B 9/127; E04B 9/18; E04B 2009/026; E04F 17/04; F21S 2/00; F21W 2131/205; F24F 7/007; F24F 13/078; H02G 3/0418; H02G 3/0437; H02G 3/263; H02G 3/381
See application file for complete search history.

(56) References Cited

U.S. PATENT DOCUMENTS

| 3,511,162 A | * | 5/1970 | Andrew ................. | F24F 3/163 454/187 |
| 3,685,235 A | * | 8/1972 | Lang ...................... | E04B 9/006 52/39 |
| 3,803,995 A | * | 4/1974 | Allander ................ | F24F 9/00 454/189 |

(Continued)

FOREIGN PATENT DOCUMENTS

DE 202015101209 U1 * 6/2016 ............ F24F 13/078

*Primary Examiner* — James M Ference
(74) *Attorney, Agent, or Firm* — Braxton Perrone, PLLC; Gregory Perrone; Bobby W. Braxton

(57) ABSTRACT

A pre-fabricated universal operating room ceiling system including red iron steel support frames and a track assembly immediately above the ceiling in the interstitial space of the operating room for supporting medical equipment including medical gas lines and electrical and data cabling and heating, ventilation and cooling trunk lines and ducts for reducing interference with such systems when installing or moving operating room equipment.

18 Claims, 12 Drawing Sheets

(56) References Cited

U.S. PATENT DOCUMENTS

| | | | | |
|---|---|---|---|---|
| 3,923,482 A * | 12/1975 | Knab | F24F 9/00 | |
| | | | 55/412 | |
| 4,506,595 A * | 3/1985 | Roberts | F24F 7/04 | |
| | | | 454/187 | |
| 4,626,747 A * | 12/1986 | Nilssen | H05B 41/245 | |
| | | | 315/161 | |
| 4,631,648 A * | 12/1986 | Nilssen | E04B 9/006 | |
| | | | 174/491 | |
| 5,424,806 A * | 6/1995 | Siegel | H05K 7/20009 | |
| | | | 15/301 | |
| 5,479,326 A * | 12/1995 | Nilssen | F21S 2/00 | |
| | | | 315/294 | |
| 5,605,423 A * | 2/1997 | Janusz | E04B 5/29 | |
| | | | 411/387.6 | |
| 5,618,090 A * | 4/1997 | Montague | A61G 12/002 | |
| | | | 312/209 | |
| 5,830,058 A * | 11/1998 | Røsjø | F24F 3/163 | |
| | | | 454/187 | |
| 5,870,450 A * | 2/1999 | Khutoryansky | A61B 6/4283 | |
| | | | 378/197 | |
| 6,010,400 A * | 1/2000 | Krainiak | A61L 2/24 | |
| | | | 454/187 | |
| 6,095,468 A * | 8/2000 | Chirico | F16M 11/2014 | |
| | | | 248/125.7 | |
| 6,110,244 A * | 8/2000 | Wood | A61G 13/108 | |
| | | | 55/385.2 | |
| 6,132,309 A * | 10/2000 | Panelli | F24F 3/167 | |
| | | | 454/187 | |
| 6,198,047 B1 * | 3/2001 | Barr | H02G 3/0456 | |
| | | | 174/101 | |
| 6,248,014 B1 * | 6/2001 | Collier | A47C 7/72 | |
| | | | 454/228 | |
| 6,439,736 B1 * | 8/2002 | Fiene | E04B 9/32 | |
| | | | 362/147 | |
| 6,464,383 B1 * | 10/2002 | Northington | A61B 90/35 | |
| | | | 362/572 | |
| 6,633,328 B1 * | 10/2003 | Byrd | H04N 7/183 | |
| | | | 348/143 | |
| 6,966,937 B2 * | 11/2005 | Yachi | B01D 46/0016 | |
| | | | 55/385.2 | |
| 7,044,851 B2 * | 5/2006 | Peterson | F24F 3/16 | |
| | | | 454/236 | |
| 8,066,802 B2 * | 11/2011 | Kristensson | A61G 13/108 | |
| | | | 95/273 | |
| 8,112,942 B2 * | 2/2012 | Bohm | E04H 3/08 | |
| | | | 52/79.1 | |
| 8,308,536 B2 * | 11/2012 | Kristensson | F24F 11/0001 | |
| | | | 454/284 | |
| 8,523,644 B2 * | 9/2013 | Melies | A61B 90/40 | |
| | | | 454/187 | |
| 8,905,585 B2 * | 12/2014 | Dallam | A61G 10/02 | |
| | | | 362/276 | |
| 9,373,943 B1 * | 6/2016 | Tannenbaum | H02G 3/0437 | |
| 9,506,266 B2 * | 11/2016 | Foldenauer | E04H 1/04 | |
| 9,671,100 B2 * | 6/2017 | Schreiber | A61B 90/30 | |
| 9,938,724 B2 * | 4/2018 | Walters | H02G 3/263 | |
| 10,071,177 B1 * | 9/2018 | Kellogg, Jr. | F24F 13/10 | |
| 10,174,961 B2 * | 1/2019 | Varley | F24F 7/00 | |
| 10,376,339 B2 * | 8/2019 | Palmerton | A61B 90/70 | |
| 2002/0174608 A1 | 11/2002 | Rapisarda | E04B 1/98 | |
| | | | 52/167.1 | |
| 2003/0002279 A1 * | 1/2003 | Fiene | E04B 9/32 | |
| | | | 362/147 | |
| 2003/0014817 A1 * | 1/2003 | Gallant | A61G 12/004 | |
| | | | 5/600 | |
| 2003/0160142 A1 * | 8/2003 | Brahler | E04B 9/006 | |
| | | | 248/317 | |
| 2004/0164220 A1 * | 8/2004 | Newkirk | A61B 50/10 | |
| | | | 248/647 | |
| 2006/0179750 A1 * | 8/2006 | Patrick | E04B 5/40 | |
| | | | 52/309.16 | |
| 2007/0180790 A1 * | 8/2007 | Lee | E04C 3/293 | |
| | | | 52/856 | |
| 2008/0000178 A1 * | 1/2008 | Hsu | E04C 3/294 | |
| | | | 52/334 | |
| 2009/0277123 A1 * | 11/2009 | Guazzo | E04B 5/29 | |
| | | | 52/698 | |
| 2011/0097986 A1 * | 4/2011 | Cursetjee | F24F 13/32 | |
| | | | 454/187 | |
| 2011/0122603 A1 * | 5/2011 | Shamshoian | E04B 9/02 | |
| | | | 362/149 | |
| 2011/0230130 A1 * | 9/2011 | Ruizlapuente | F24F 3/163 | |
| | | | 454/187 | |
| 2012/0293309 A1 * | 11/2012 | Spiro | F21S 8/06 | |
| | | | 340/12.32 | |
| 2013/0182417 A1 * | 7/2013 | Amat Girbau | F21V 21/02 | |
| | | | 362/147 | |
| 2014/0273803 A1 * | 9/2014 | Fontanesi | F24F 13/078 | |
| | | | 454/293 | |
| 2014/0293622 A1 * | 10/2014 | Hauschulte | F21V 3/00 | |
| | | | 362/364 | |
| 2014/0355248 A1 * | 12/2014 | Cursetjee | F24F 13/078 | |
| | | | 362/96 | |
| 2015/0055323 A1 * | 2/2015 | Schreiber | F21V 21/30 | |
| | | | 362/96 | |
| 2016/0258165 A1 * | 9/2016 | Walters | E04B 9/006 | |
| 2016/0263266 A1 * | 9/2016 | Wesen | A61L 9/20 | |
| 2017/0003015 A1 * | 1/2017 | Schreiber | A61B 90/30 | |
| 2017/0101778 A1 * | 4/2017 | Schreiber | A61B 90/40 | |
| 2018/0256280 A1 * | 9/2018 | Schreiber | A61B 90/35 | |
| 2018/0355610 A1 * | 12/2018 | Awasthi | E04B 9/067 | |
| 2019/0234645 A1 * | 8/2019 | Haar | F24F 7/06 | |
| 2019/0257081 A1 * | 8/2019 | Heatly | E04B 1/04 | |
| 2020/0248449 A1 * | 8/2020 | Hodsden | E04B 9/006 | |

* cited by examiner

UNIVERSAL PRE-FABRICATED OPERATING ROOM CEILING SYSTEM

PRIORITY

This application claims priority to pending U.S. Provisional Patent Application No. 62/801,879 filed Feb. 6, 2019, the entirety of which is incorporated herein by reference.

TECHNICAL FIELD

This disclosure relates a universal system to accommodate the interstitial space of an operating room setting.

Traditionally, when a hospital or outpatient surgical facility wishes to improve, relocate or add surgical room equipment that is ceiling mounted or interfaced with equipment located in the interstitials space of the operating room, the operating room must be closed for extended periods of time while the new equipment is placed or the improvement is executed. With this traditional approach comes the placement of containment barriers and opening or full-scale removal of the ceiling of the operating room. The ceiling above the surgical table location must be cleared to accommodate placement for other equipment that supports the new equipment, such as structural supports as well as medical gas lines, power cables and communication lines. Pre-existing support structures and gas lines, power cables and communication lines, however, are in the way and often prevent placement of new cabling, etc. unless they are re-routed.

Another approach is described in U.S. Pat. No. 9,938,724 to Walters. Walters describes an operating room ceiling system that is adaptable to accommodate existing equipment, cabling and gas lines in an operating room setting. The Walters operating room ceiling system includes an air diffuser assembly, a raceway assembly, and a light assembly. The raceway assembly is positioned along an outer perimeter of the air diffuser assembly. The light assembly is positioned along an outer perimeter of the raceway assembly. The raceway assembly is configured to provide a raceway to facilitate routing of cables, medical gas lines, and electrical conduit for electrical power.

Neither of these approaches is desirable for various reasons. First, the operating room may have to be shut down for an extended period of time for the modifications. As a result, revenue that would have been generated for the surgical facility during renovation is lost. Moreover, such a renovation is relatively expensive and potential obstacles above an operating room ceiling may prevent locating new equipment in a desired location as planned. For example, heating, ventilation and cooling (HVAC) ductwork and components are significant obstacles to relocation of physical support structures or cabling and gas lines. Further, even for the retrofit system described in the Walters patent, significant interference with surgical space use is encountered. In this respect, the Walters system is not a purely universal unit. That is, it must be custom fabricated according to the dimensions and other environmental variables of the particular operating room in which it is to be installed. This customization also results in considerable expense and causes the provider of these customized systems to accommodate obstructions such as HVAC components or other building structures. What is needed is a universal, flexible solution installed during operating room facility construction that does not interfere with or prohibit utilization of the operating room and at the same time can accommodate virtually any surgical equipment configuration, future changes to the type and location of the surgical equipment, as well as building infrastructure requirements.

SUMMARY

The presently described universal operating room ceiling system includes red iron or other tubular steel support structures installed on operating room facility concrete structural components of the building. All components of an operating room including structural components, medical gas lines, electrical and data lines and heating, ventilation and cooling equipment are accommodated by the presently described universal system that is largely assembled offsite from the operating facility, greatly reducing labor and installation costs. The system provides flexibility for future positioning, repositioning and placement of operating room equipment and associated medical gas lines and power requirements. A track assembly is positioned on a pre-fabricated grid directly above the ceiling in the interstitial space. A ceiling assembly includes air diffusers and lighting fixtures. The track assembly is configured to provide access to facilitate routing of cables, medical gas lines, and electrical conduit for electrical power. Advantages offered by the system of the present invention include (a) the system is a pre-fabricated system; (b) the elevated track assembly allows for ceiling-mounted equipment placement anywhere within the system without conflict; (c) elevating the track assembly allows for standardizing the size of the system as the system does not have to compete for space with lights and diffusers on the ceiling; (d) the system allows for easier installation as compared to conventional systems; and (e) the aesthetic appearance of the track assembly is of less importance because it is elevated.

BRIEF DESCRIPTION OF THE DRAWINGS

The present invention is illustrated by way of example and is not limited by the accompanying figures, in which like references indicate similar elements. Elements in the figures are illustrated for simplicity and clarity and have not necessarily been drawn to scale.

DETAILED DESCRIPTION

Figure 1:
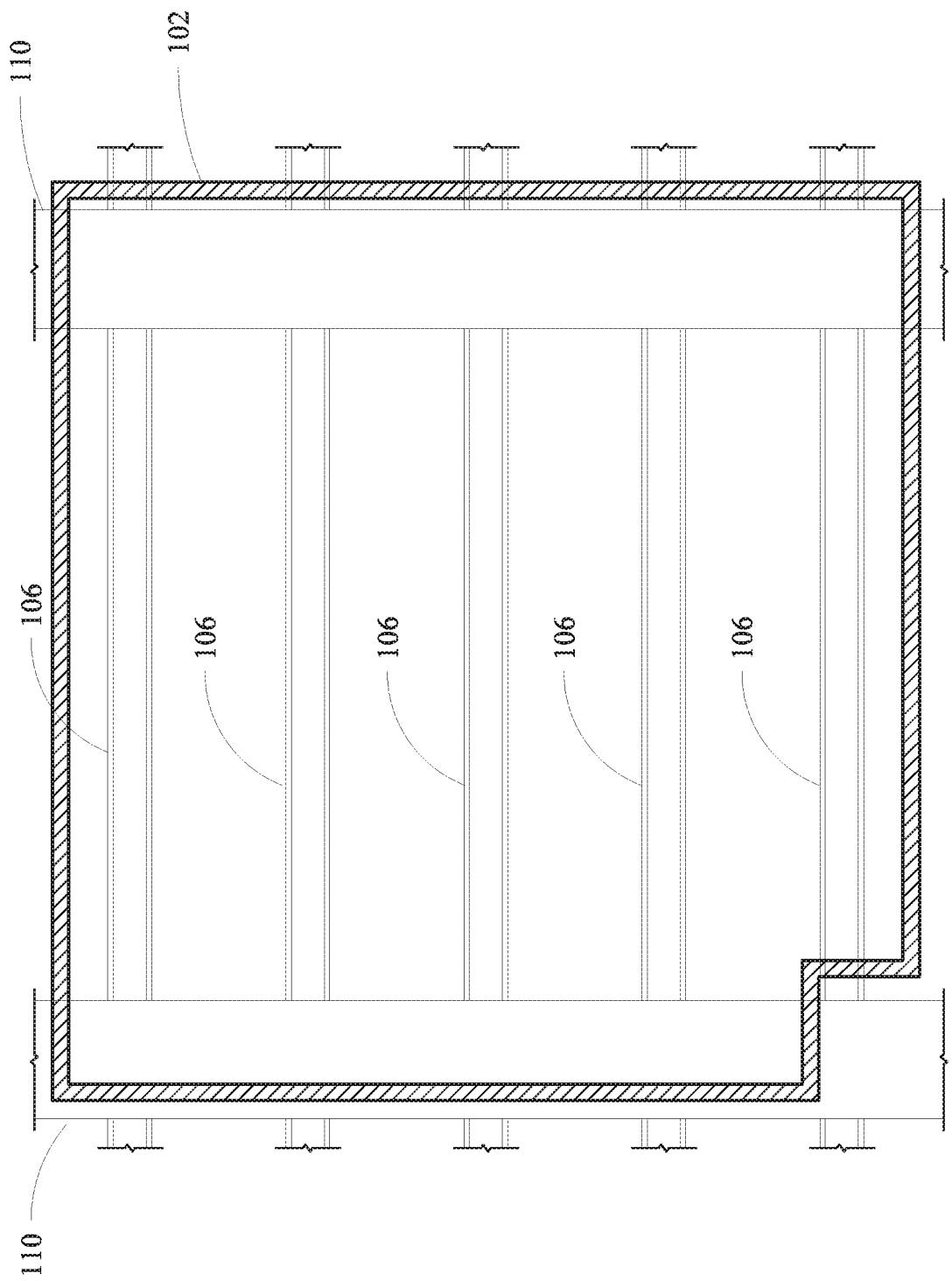
FIG. 1 depicts a building with multiple floors in which an operating room ceiling system will be installed according to one embodiment of the present disclosure.

In the following detailed description of exemplary embodiments of the invention, specific exemplary embodiments in which the invention may be practiced are described in sufficient detail to enable those skilled in the art to practice the invention, and it is to be understood that other embodiments may be utilized and that architectural, mechanical, electrical and other changes may be made without departing from the spirit or scope of the present invention. The following detailed description is, therefore, not to be taken in a limiting sense, and the scope of the present invention is defined only by the appended claims and their equivalents. According to the present disclosure, new construction of an operating room can be performed in a universal and flexible manner by installation of a ceiling system frame and grid that efficiently accommodates the various operational components of a surgery facility. By fabricating most of the universal ceiling system off-site from the surgical facility a significant reduction in installation labor costs and facility down time is achieved. A reduced amount of time and lower expense is advantageous over conventional approaches such as retrofitting operating room ceiling systems into existing space or building an on-site custom ceiling system for new installs.

An operating room equipped with the presently described ceiling system can accommodate changes in operating room procedures and be readily adapted for new equipment required for operating room upgrades as well as new equipment locations. In one embodiment, the presently described ceiling system is positioned to occupy the area in an operating room ceiling above a surgical table. Optionally, in an embodiment an operating room ceiling system includes air diffusers that provide clean air directly over a patient (and surgical staff) in a sterile field as well as light fixtures.

In various embodiments, a rectangular track assembly made of a variety of materials including plastic and sheet metal is positioned above the ceiling vertically between ceiling level air diffusers and light fixtures and HVAC duct work. The track is a rectangular or tubular trough that houses medical gases needed in the operating room as well as electrical and data lines. The track assembly of the present invention is comprised of various sections in one embodiment, including at least one removable or closeable access panels on the bottom of the track that is substantially parallel to the ceiling below. In another embodiment, the track includes openings at various intervals allowing access to medical gas lines and electrical and data lines contained therein. In various embodiments, components enter a desired area in the track assembly and are then distributed to where ceiling mounted equipment is to be located. In one or more embodiments, the ceiling mounted equipment is mechanically coupled to a structural support by an intermediate structure that receives a portion of the track assembly and includes an equipment mounting plate. The track assembly allows medical gas lines, electrical cables, and communication cables to be readily rerouted if the ceiling mounted equipment is moved or upgraded or additional ceiling mounted equipment is added. The disclosed techniques generally result in lower installation cost, faster turn around time, and minimal to no containment is required during an equipment upgrade.

With the track assembly and complete structural support positioned above the ceiling, equipment can be placed anywhere in the area within the ceiling system frame and grid. If new equipment is required to be installed, the location of the new equipment is not limited by the placement of the old equipment and can be located anywhere within the frame and grid. The footprint of the track assembly and structural support covers the operating area within the operating room, which is typically the center of the room, and can extend outward from the room's center. The lighting installed in the universal frame and grid provides ample lighting of the patient area, access to ceiling mounted equipment, and one or more light fixtures can be readily removed to provide access to the track assembly. In addition, the air diffuser provides a clean patient area.

Optionally, the ceiling assembly can include air diffusers used to circulate clean air over an operating table. For example, the air diffuser assembly can include a plurality of high-efficiency particle absorption (HEPA) filtered air vents or non-HEPA filtered air vents.

A support structure integrated above the ceiling is configured to support the operating room ceiling system and ceiling mounted surgical equipment (anesthesia booms, surgical lights, etc.) via modular steel rails, such as Hilti brand rails. In various embodiments, surgical equipment may be positioned anywhere within the ceiling frame and grid system. According to various aspects of the present disclosure, additional surgical equipment can be added with little to no structural support cost by simply making medical gas lines and electrical and data cabling available through the track assembly and structurally attaching the added equipment to the modular steel rails. The presently described ceiling system can be readily re-configured as needed. For example, removable bottom panels of the track assembly can be relocated to another location on the track assembly (or replaced with new panels) when various equipment requires relocation.

In various embodiments, communication cables are pulled into the track assembly and routed to specific equipment. In one or more embodiments, medical gas is hard piped to a top wall of the track assembly and a hose inside the track assembly is employed to deliver the gas to a desired location. Similarly, power is provided inside the track assembly and conduit (rigid or flexible) and junction-boxes can be employed to distribute power throughout the track assembly.

The track assembly can be used to distribute medical gas lines, power cables, and/or communication cables to various ceiling mounted surgical equipment, as well as any other devices that are incorporated into the track assembly. In one or more embodiments, the track assembly includes several sheet metal or plastic track boxes FIG. 1 depicts a surgical facility that can be a multi-floored building, having beams 106 within planned operating room 102. Beams 106 can span multiple operating rooms or can run between walls of an operating room. Beams 106 are typically spaced as much as several feet apart from either the front to back of the footprint of facility or from the left interior wall to right interior wall of the space. As shown in FIG. 1, beam 106 runs between structural beams 110 on each side of the operating room 102. Structural beams 110 can be composed of either concrete or steel. In commercial buildings, such as those that will house a surgical facility, beams 106 are typically constructed of concrete, but can also be constructed of steel.

Figure 2:
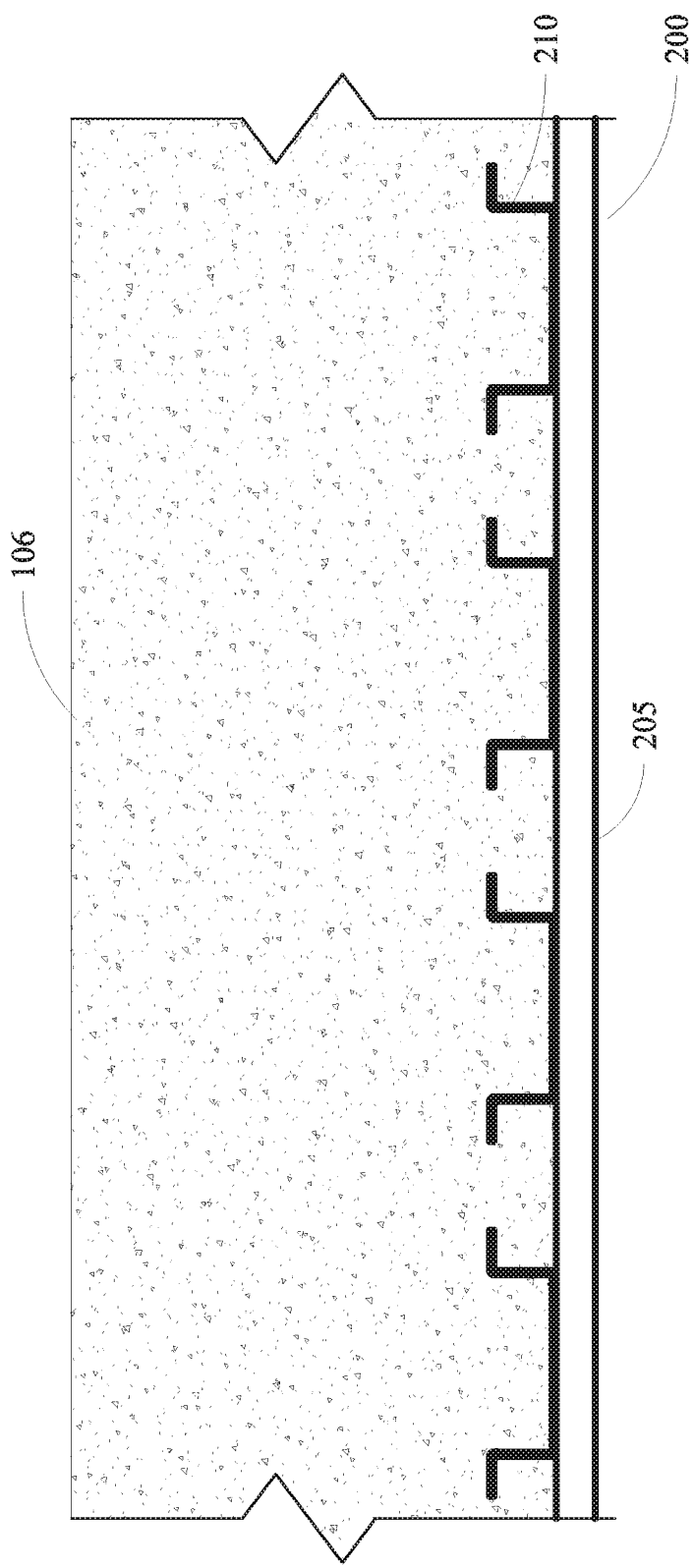
FIG. 2 illustrates an embedded operating room ceiling system support according to one embodiment of the present disclosure.

FIG. 2 depicts an embedded steel red-iron frame connector used when beams 106 are made of concrete. In FIG. 2, embedded connector 200 is an elongated steel strip that runs a substantial portion of the length of beam 106 to which a red-iron frame will be connected. Embedded connector 200 includes a plurality of headed spikes 210 substantially evenly spaced along plate or strut 205. Headed spikes 210 are embedded into concrete beam 106. In one embodiment the entire length of each headed spike is embedded in the concrete beam with plate or strut 205 exposed. Once installed on beam 106, plate or strut 205 is secured flush with beam 106. As will be discussed, each red-iron frame is installed on beam 106 via embedded connector 200 at plate 205 and other suitable connection methods in the case of a strut. Primarily, connection of the red-iron frame to embedded connector is achieved by welding at a point P to a modular steel interface plate as discussed below.

Figure 3:
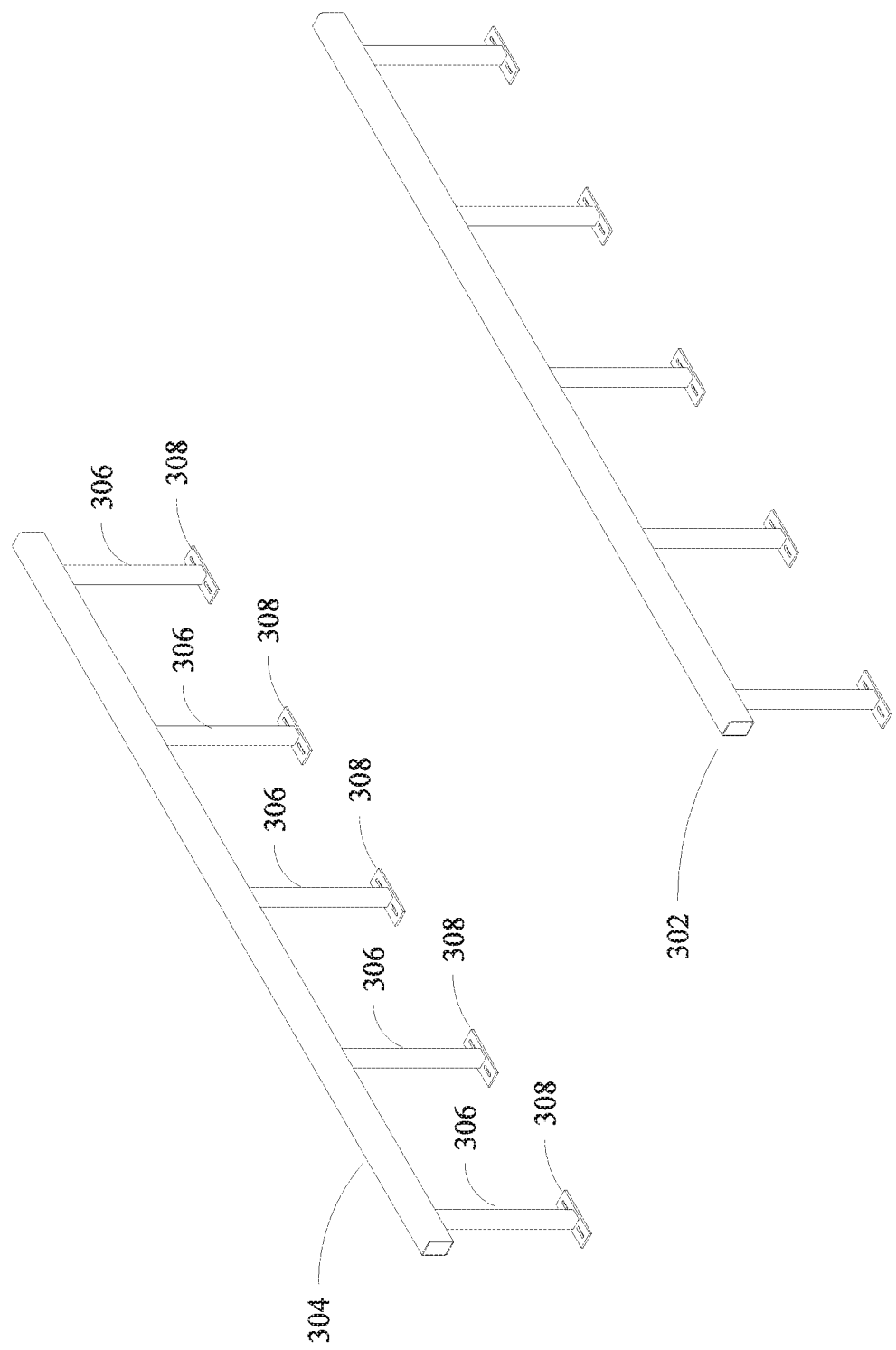
FIG. 3 depicts multiple red-iron frames of the operating room ceiling system according to an embodiment of the present disclosure.
Figure 5:
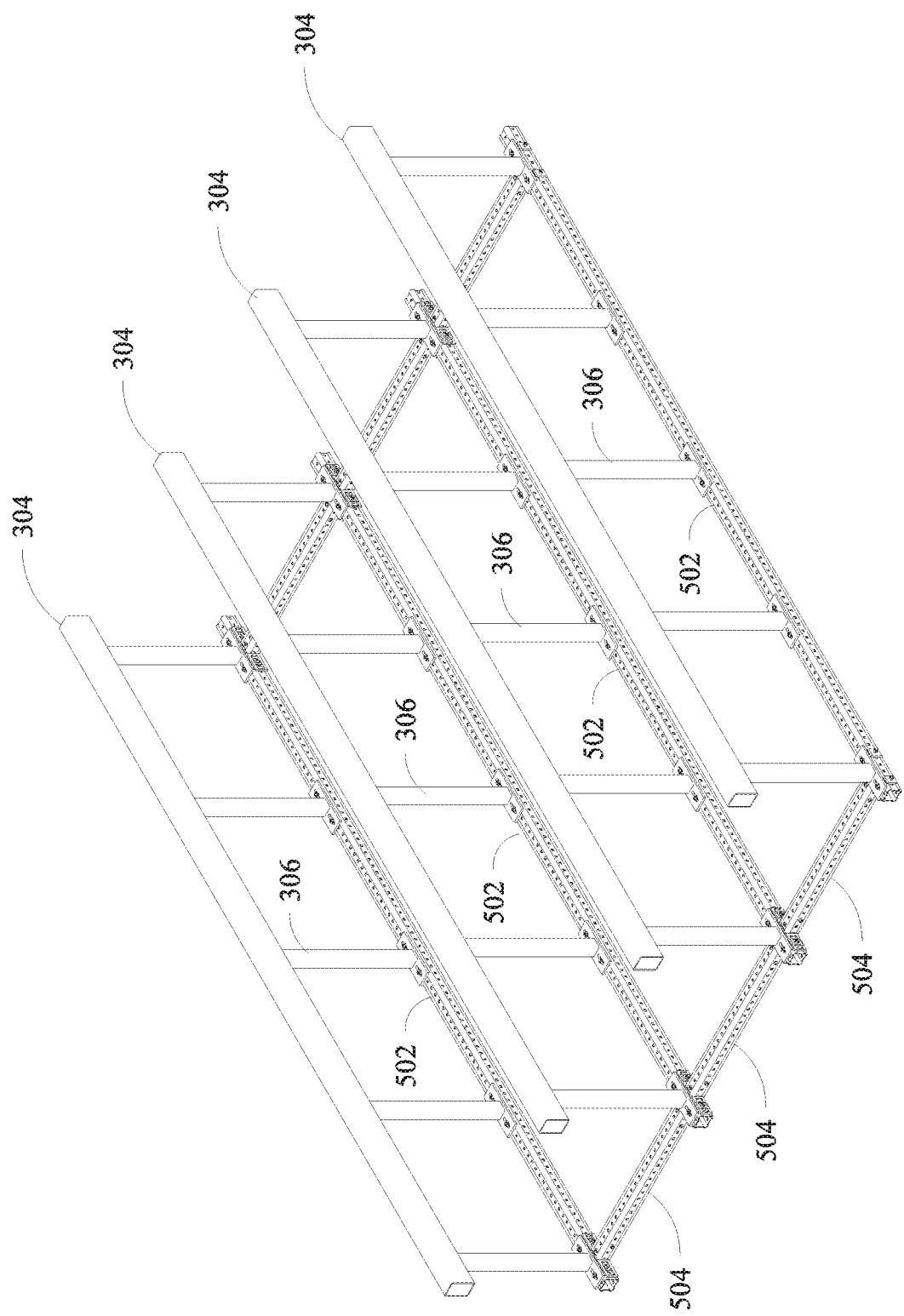
FIG. 5 depicts a grid of red-iron frames and modular steel rails according to an embodiment of the present disclosure.

FIG. 3 depicts a pair of red-iron frames according to an embodiment of the present invention. In FIG. 3, red-iron frame 302 comprises a main horizontal span 304. In one embodiment of the red-iron frame, vertical members 306 are evenly spaced and affixed to the underside of span 304. That is, in the operating room environment, vertical members 306 point towards the floor of the operating room below. At the distal and of each vertical member 306 is modular steel interface plate 308. Modular steel interface plate 308 connects red iron frame 302 to long modular steel rails 502 and modular steel cross rails 504 as shown in FIG. 5. As is known in the art, red iron is a structural steel manufactured with no rust coating or with only a red oxide coating. The red iron frames 302 employed in the presently described ceiling system are not visible to occupants of the building and are not exposed to the outdoors or not otherwise intended to be exposed to moisture. The frames 302, however, must be of significant structural strength to support the various medical equipment, including booms and columns, HVAC, track assembly, lighting and modular steel rails which suspend from it when installed. A mounting plate for the various medical equipment disposed in the operating room is used to secure the medical equipment to the modular steel rails (502 of FIG. 5).

Figure 4A:
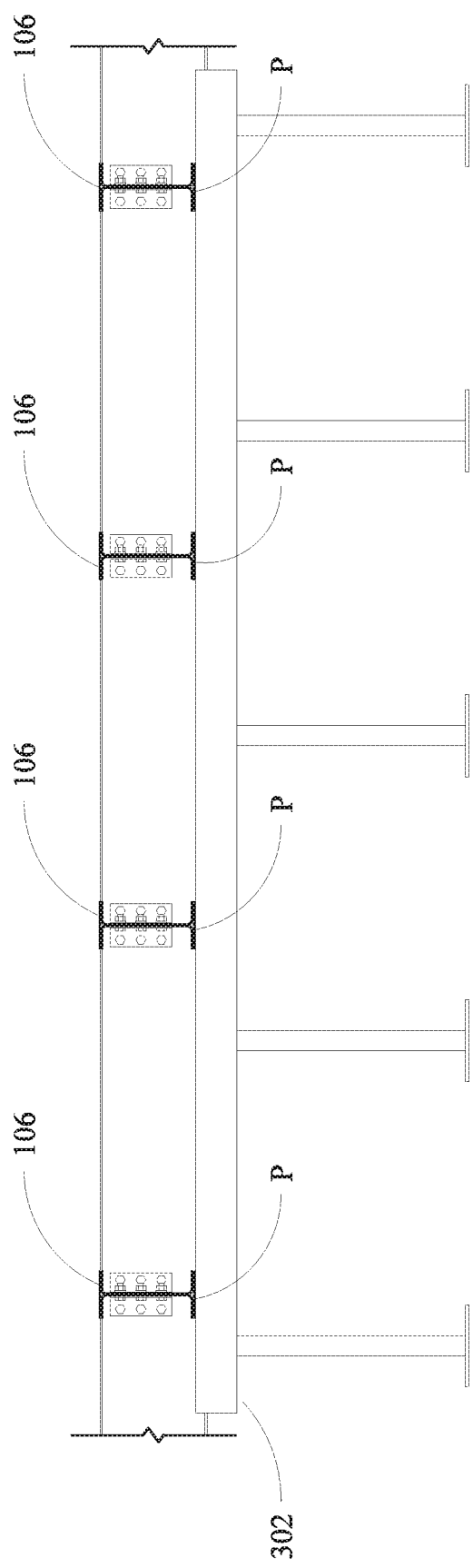
FIG. 4A depicts installation of a red-iron frame on an embedded operating room ceiling system support installed in a steel ceiling beam arrangement of an operating room according to an embodiment of the present disclosure.

FIGS. 4A through 4D depict various embodiments for attaching red iron frame 302 to different operating room ceiling configurations. In FIG. 4A, beam 106 comprises a steel beam and horizontal span 304 of red iron frame 302 can be attached to beam 106 directly by welding the two at various points P along beam 106.

Figure 4B:
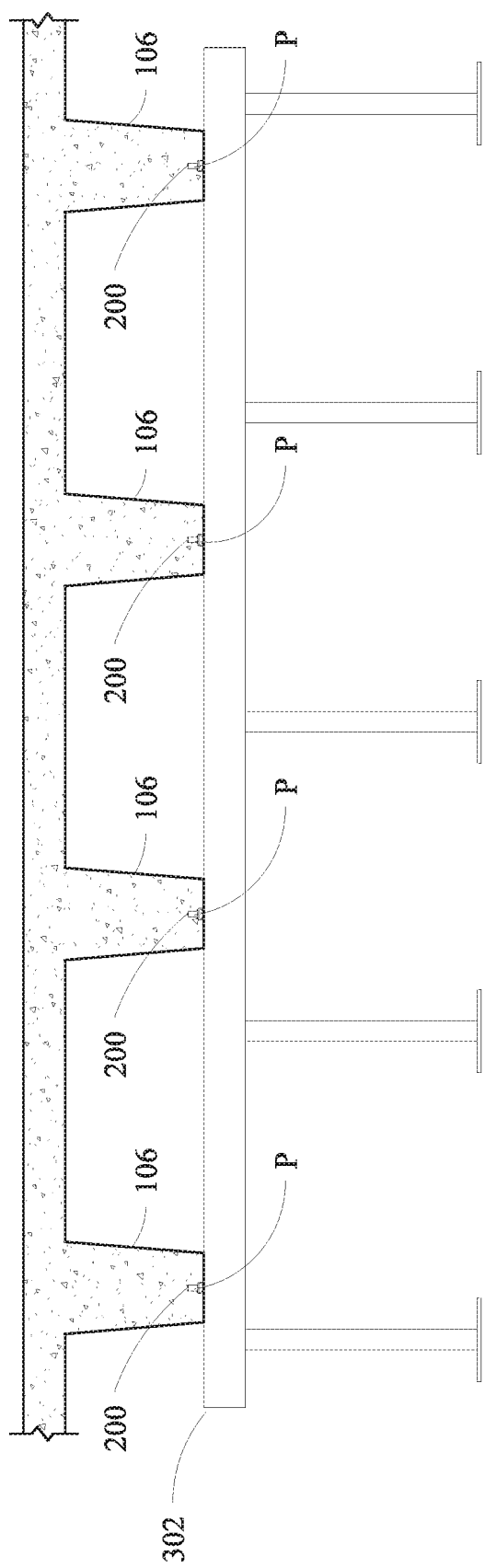
FIG. 4B depicts installation of a red-iron frame on an embedded operating room ceiling system support installed in a concrete ceiling beam of an operating room according to an embodiment of the present disclosure.

In FIG. 4B, beams 106 are concrete and are attached to red iron frame 302 at points P via embedded connector 200 (FIG. 2). Referring back to FIG. 2, plate or strut 205 has an associated plurality of spikes 210 that are embedded within the concrete to hold embedded connector 200 in place. In FIG. 4B, red iron frame 302 is attached to embedded connector 200, which can cross several concrete beams or joists 106. Red iron frame 302 is attached to embedded connector 200 at various points P. Connection can be achieved by welding or other suitable attachment device or process. As shown in FIG. 2, embedded connector is installed on concrete beam 106 by embedding headed spikes 210 into concrete beam 106. Once fully inserted and secured with concrete or other suitable adhesive, plate 205 is flush against the bottom face of beam 106. As installed, plate 205 is constructed of steel and provides an interface for connecting red iron frame 302 to beam 106 through methods such as welding or other suitable fastening techniques. Optionally, other fastening devices, such as an L-bracket (FIG. 4C), can be attached to connect plate 205 to red iron frame 302. The steel construction of plate 205 allows for connection of red iron frame to beam 106 by welding the red iron frame 302 to plate 205 at points P along horizontal span 304 as shown. The connection of red iron frame 302 across two or more beams 106 provides a structurally strong support for connection of equipment anywhere within the footprint of the operating room. As shown, the pair of embedded connectors 200 are substantially parallel to each and perpendicular to red iron frames 302.

Figure 4C:
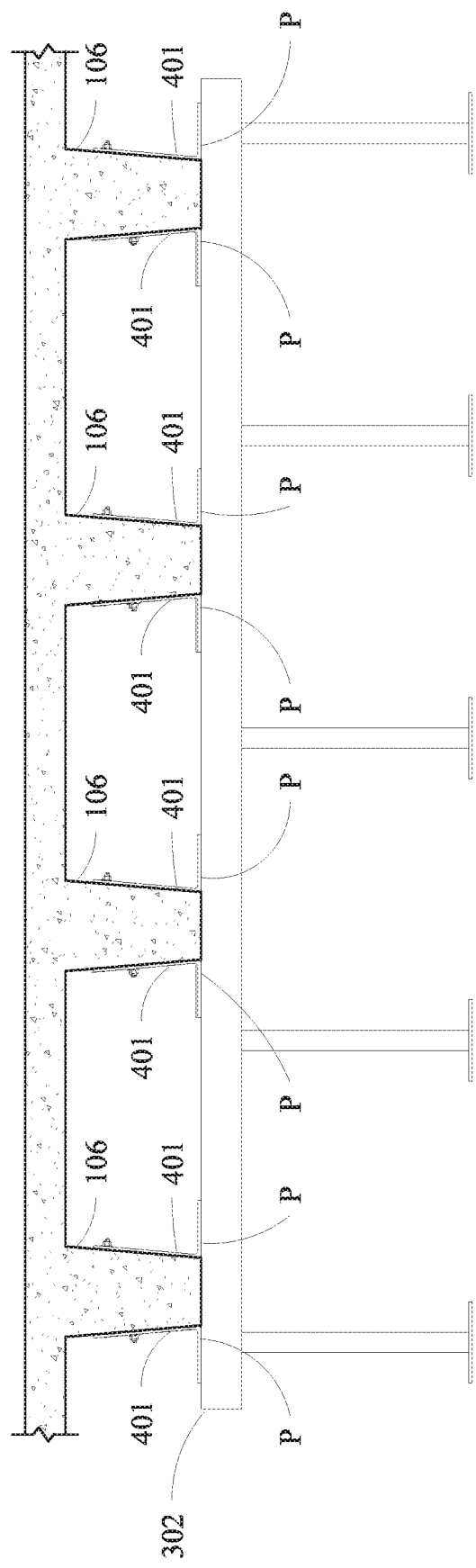
FIG. 4C depicts installation of a red-iron frame on an embedded operating room ceiling system support installed in a concrete ceiling beam of an operating room according to an embodiment of the present disclosure.

FIG. 4C depicts a beam 106 as in FIG. 4B but in this embodiment, L-shaped brackets 401 are affixed to each side of beam 106, which in this embodiment is also concrete. The horizontal leg of L-shaped bracket 401 is welded red iron frame at points P as shown or by other suitable attachment device or process. The vertical leg of L-shaped bracket 401 is affixed to the side of beam 106 by stable bolts.

Figure 4D:
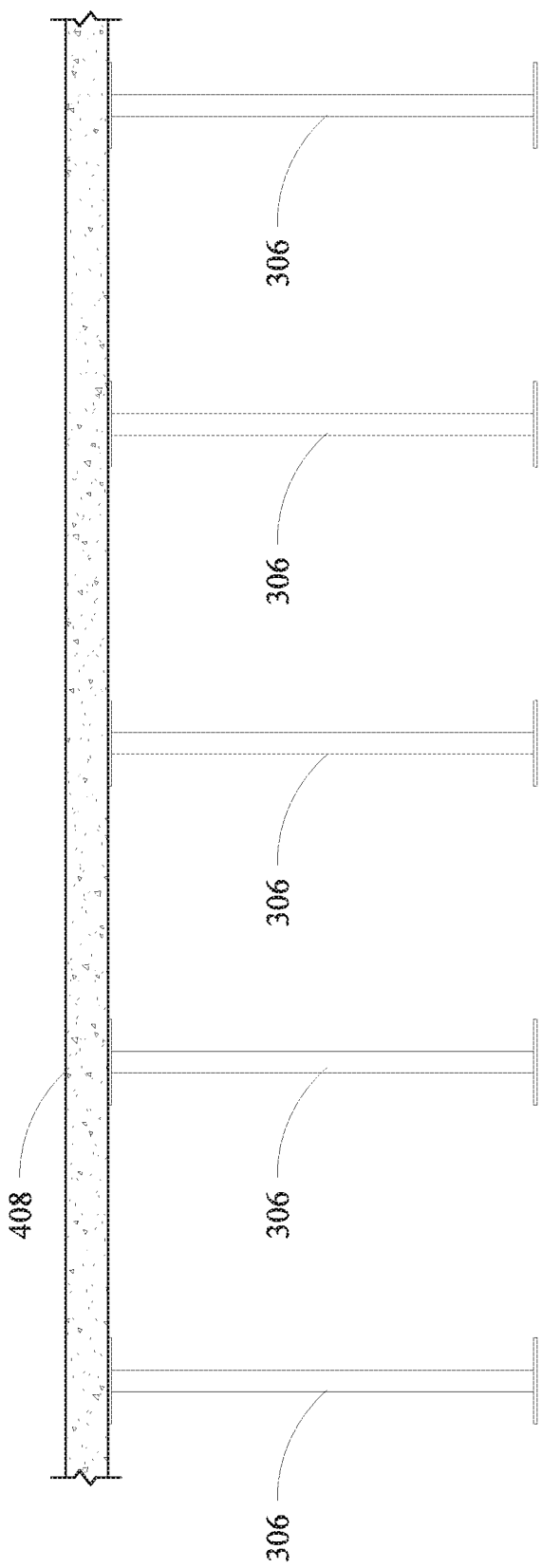
FIG. 4D depicts installation of a red-iron frame on an embedded operating room ceiling system support installed in a concrete ceiling of an operating room according to an embodiment of the present disclosure.

FIG. 4D depicts direct connection of red iron vertical members 306 to substantially flat concrete ceiling 408. In this embodiment, anchors can be used to secure red iron vertical members 306 at various points on ceiling 408. As described in connection with FIG. 3, modular steel interface plate at the bottom or distal end of vertical member 306 is used to connect long modular steel rails 502 and modular steel cross rails 504 (FIG. 5).

FIG. 5 depicts a red iron frame and grid assembly formed by connection of various red-iron frames 302 and a plurality of modular steel rails comprising long modular steel rails 502 and modular steel cross rails 504. As shown, the distal end of vertical leg 306 of each red iron frame 302 is connected to long modular steel rails 502 and modular steel cross rails 504. As can be seen in the figure, four such red iron frames 302 are arranged in parallel to each other and evenly spaced. Long modular steel rails 502 are connected to each vertical leg 306 so as to form a rectangular grid. Horizontal connection of long modular steel rails 502 by modular steel cross rails 504 can be but are not necessarily uniform, and can accommodate location of various devices and systems within the environment. In one embodiment, horizontal span 304 of each red iron frame 302 is connected to embedded connector 200 installed on cement beam 106 at various points P (see FIG. 4). With the arrangement of modular steel rails 502 and vertical legs 306, a strong frame and grid is formed that is ideal for supporting various components to support operating room medical equipment, HVAC, medical gas, lighting and other requirements. In addition, the frame and grid arrangement such as that described and depicted in connection with FIG. 5 can be assembled off site and universally installed in new construction or demolished surgical facility space, saving time and labor costs.

Figure 6:
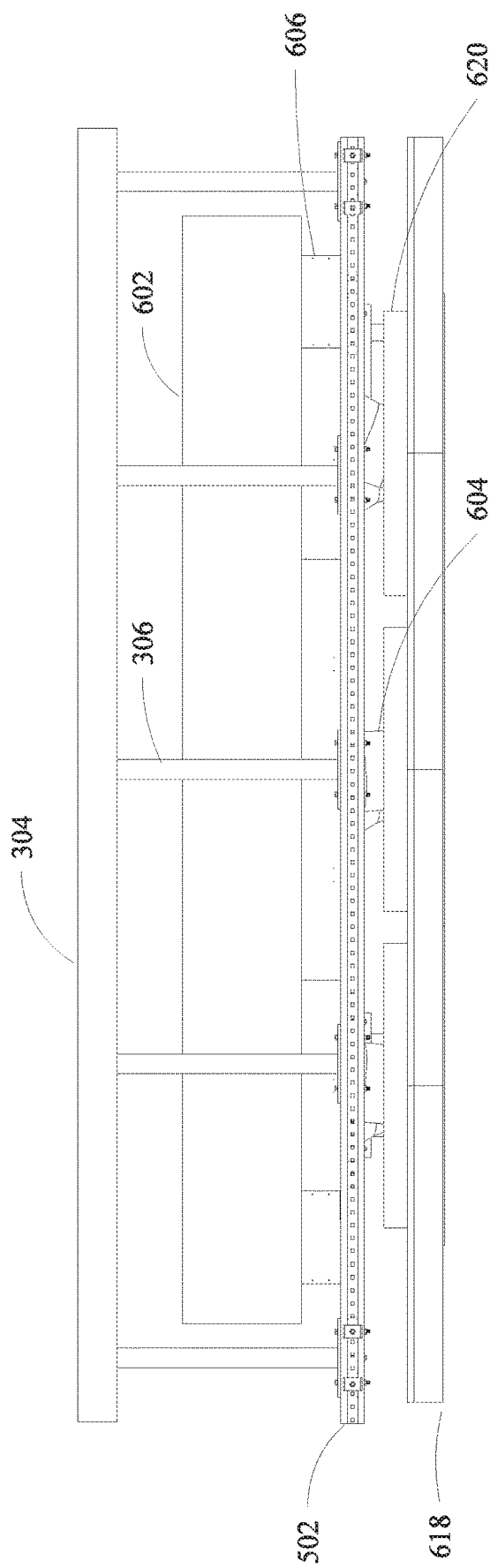
FIG. 6 depicts a side view of a track and heating, cooling and ventilation equipment supported by the grid of red-iron frame and modular steel rails according to an embodiment of the present disclosure.

The modular steel rails 502 can be connected to the vertical legs 306 as shown in FIG. 5 by a variety of means. In one embodiment, modular steel rails 502 include a plurality of slots or apertures sized to receive a bolt or screw for adhering modular steel rail 502 to another structure and connecting other objects or structures to modular steel rail 502. FIG. 6 depicts a side view of a partially assembled operating room ceiling system according to an embodiment of the present invention. As shown in FIG. 6, the red iron frame and grid arrangement comprising the modular steel rails 502 connected to red iron frame vertical legs 306 (as assembled in FIG. 5) serves as the support structure for HVAC duct work, diffusers and a track assembly for housing medical gas lines and electrical and data lines. In one embodiment, track assembly 606 is arranged directly above modular steel rails 502 that are placed as a grid as discussed in connection with FIG. 5. That is, the track assembly is positioned above a ceiling assembly in the interstitial space of an operating room for supporting medical equipment. Track assembly 606 can be rectangular in shape and tubular and provided in sections for ease of installation and assembly. Alternatively, track assembly 606 can take other shapes or forms to accommodate and support the equipment that will reside in the operating room and corresponding medical gas, electrical and data lines. In one embodiment, track assembly 606 is arranged as a rectangle extended near the perimeter of the grid formed by modular steel rails 502. In this manner, track assembly 606 extends throughout the space of the subject operating room.

Also shown in FIG. 6 is an HVAC trunk line 602 installed above track assembly 606. Trunk line 602 includes multiple ports to which HVAC ducts 604 are connected in order to provide adequate air circulation to the operating room. A lower end of HVAC duct 604 is connected to ceiling assembly 618 that includes diffuser 620 through which recirculated and filtered air is returned to the operating room. Ceiling assembly 618, optionally including diffuser 620 in one embodiment is flush with the interior ceiling of the operating room. Optionally, ducts 604 as will be discussed can reside within the interior of the rectangle formed by track assembly 606 in order to avoid interference with operating room equipment connection to medical gas lines and electrical and data cables both during new construction and later repositioning or adding or removal of equipment. That is, the duct ports preinstalled in trunk line 602 face the interior of the grid formed by the modular steel rails 502 and the corresponding HVAC ducts 604 will connect to air diffusers located within the perimeter of track assembly 606.

Figure 7:
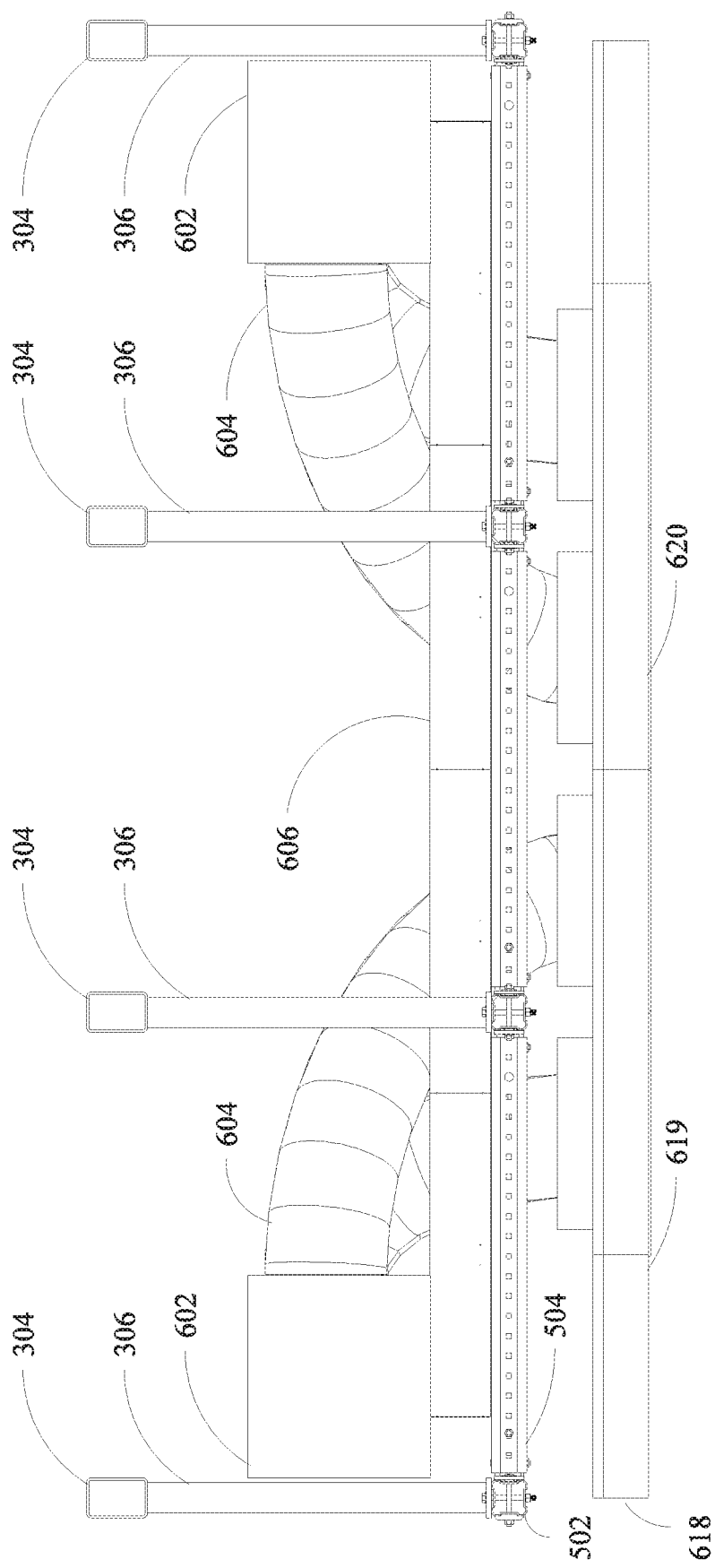
FIG. 7 depicts an alternative side view of a track and heating, cooling and ventilation equipment supported by the grid of red-iron frame and modular steel rails according to an embodiment of the present disclosure.

FIG. 7 provides an alternate view of the assembled operating room ceiling system of the present invention. FIG. 7 provides a second side view of a partially assembled operating room ceiling system according to an embodiment of the present invention. As shown in FIG. 7, the red iron frame and grid arrangement comprising the modular steel rails 502 connected to red iron frame vertical legs 306 (as assembled in FIG. 5) serves as the support structure for medical equipment, HVAC duct work, diffusers and a track assembly for housing medical gas lines and electrical and data lines and provides structural support for medical equipment. As shown in this view, track assembly 606 is arranged directly above modular steel rails 502 that are placed as a grid as discussed in connection with FIG. 5. Track assembly 606 can be rectangular and tubular in shape and provided in sections for ease of installation and assembly. In one embodiment, track assembly 606 is arranged as a rectangle extending close to the perimeter of the grid formed by modular steel rails 502.

Also shown in FIG. 7 are HVAC trunk lines 602 installed above track assembly 606. Trunk lines 602 includes multiple ports to which HVAC ducts 604 are connected in order to provide adequate air circulation to the operating room. A lower end of each HVAC duct 604 is connected to ceiling assembly 618 having at least one diffuser 620 through which recirculated and filtered air is returned to the operating room. Ceiling assembly 618 and diffuser 620 in one embodiment is flush with the interior ceiling of the operating room. Ducts 604 as will be discussed reside within the interior of the rectangle formed by track assembly 606 in order to avoid interference with operating room equipment connection to medical gas lines and electrical and data cables both during new construction and later repositioning or adding or removal of equipment. That is, the duct ports preinstalled in trunk line 602 face the interior of the grid formed by the modular steel rails 502. The corresponding HVAC ducts 604 will connect to air diffusers located within the perimeter of track assembly 606.

In one embodiment, track assembly 606 supports attachment of medical columns or booms through which hoses carrying medical gas, as well as electrical cables, data cables, etc. In at least one embodiment, ceiling assembly 618 includes one or more diffusers 620 that can be HEPA diffusers. Ceiling assembly 618 in one embodiment can also include light assembly 619 as shown in FIG. 7. As seen in the various figures, track assembly 606 is positioned directly above the grid formed by modular steel rails 502 and 504 (FIG. 5). Above and to the outside of track assembly 606 are HVAC trunk lines 602. Below track assembly 606 is ceiling assembly 618. Ceiling assembly 618 in one embodiment comprises a number of separate panels of typical dimensions for commercial ceiling tiles. Some of these separate panels can be diffuser panels 620 and lighting panels 619. Optionally, lighting panels 619 can include a plurality of troffers, including, LED, fluorescent, or incandescent troffers.

Figure 8:
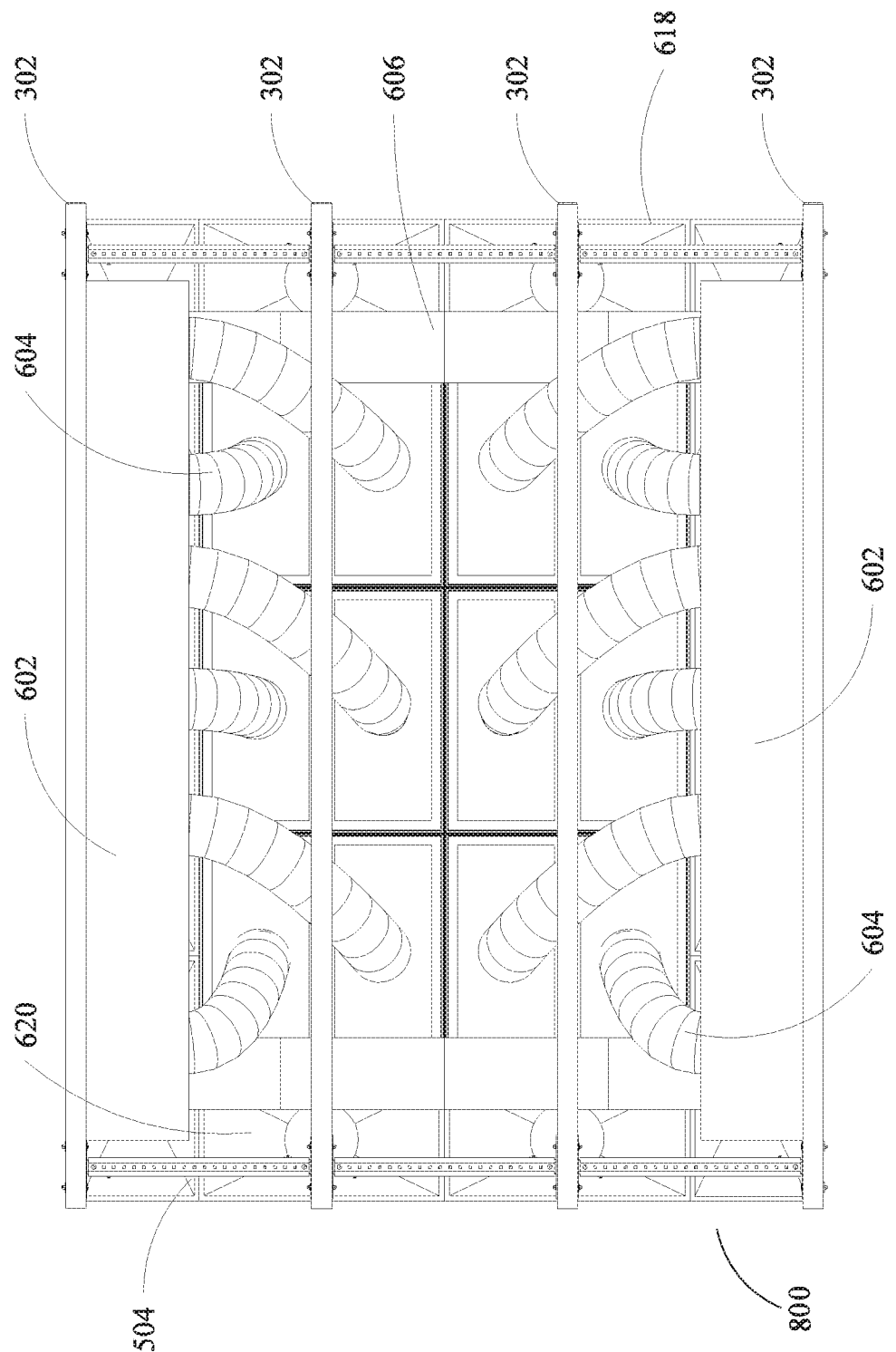
FIG. 8 depicts an overhead view of an assembled operating room ceiling system according to an embodiment of the present disclosure.

FIG. 8 provides a top view of the completed universal operating room ceiling system 800 according to an embodiment of the present invention. In FIG. 8, the frame and grid arrangement comprising red iron frames 302 and modular steel rails 502 and 504 serve as the platform for ceiling system 800. Attached directly above the grid formed from steel rails 502 and 504 is track assembly 606. Track assembly 606 will house and serve as an access point for connection of medical gas lines, as well as electrical and data cabling. Track assembly 606 can be a continuous and substantially hollow in various shapes to surround the operating room environment in one embodiment. In another embodiment, one or more non-continuous track assemblies maybe arranged at various locations within the operating room to provide the necessary access. Several such non-continuous track assemblies can surround the operating area as would the continuous track assembly. If multiple track assemblies are used, at least one is positioned above the ceiling assembly in the interstitial space of an operating room for supporting medical equipment. Above track assembly 606 are a pair of HVAC trunk lines 602. These trunk lines 602 act as the interface to facility HVAC equipment that carries cooled and heated air to the operating space. By making trunk lines 602 a part of the pre-fabricated and universal operating room ceiling system 800, complicated coordination involved in dealing with pre-installed HVAC ducts and medical equipment placed by a variety of vendors and sourced to a wide range of manufacturers is removed. Each trunk line 602 includes ports from which ducts 604 emanate. Ducts 604 end at diffuser panels 620 located within ceiling assembly 618. Ceiling assembly 618 is the ceiling portion of system 800 that is in direct contact with the operating room. That is, ceiling assembly 618 at least in part serves as the physical ceiling in the operating room.

Optionally, various lighting assemblies 619 can be located in ceiling assembly 618. The diffusers 620 and lighting assemblies 619 within ceiling assembly 618 may be arranged in various ways, most specifically to direct lighting to necessary areas according to the arrangement of a particular operating room. The modular nature of ceiling assembly 618 makes movement of diffusers and lighting panels relatively simple. Note in FIG. 8 that ducts 604 reside within the perimeter of track assembly 606 in order to isolate duct work and reduce interference with initial installation or subsequent modification of operating room equipment or equipment location.

Figure 9:
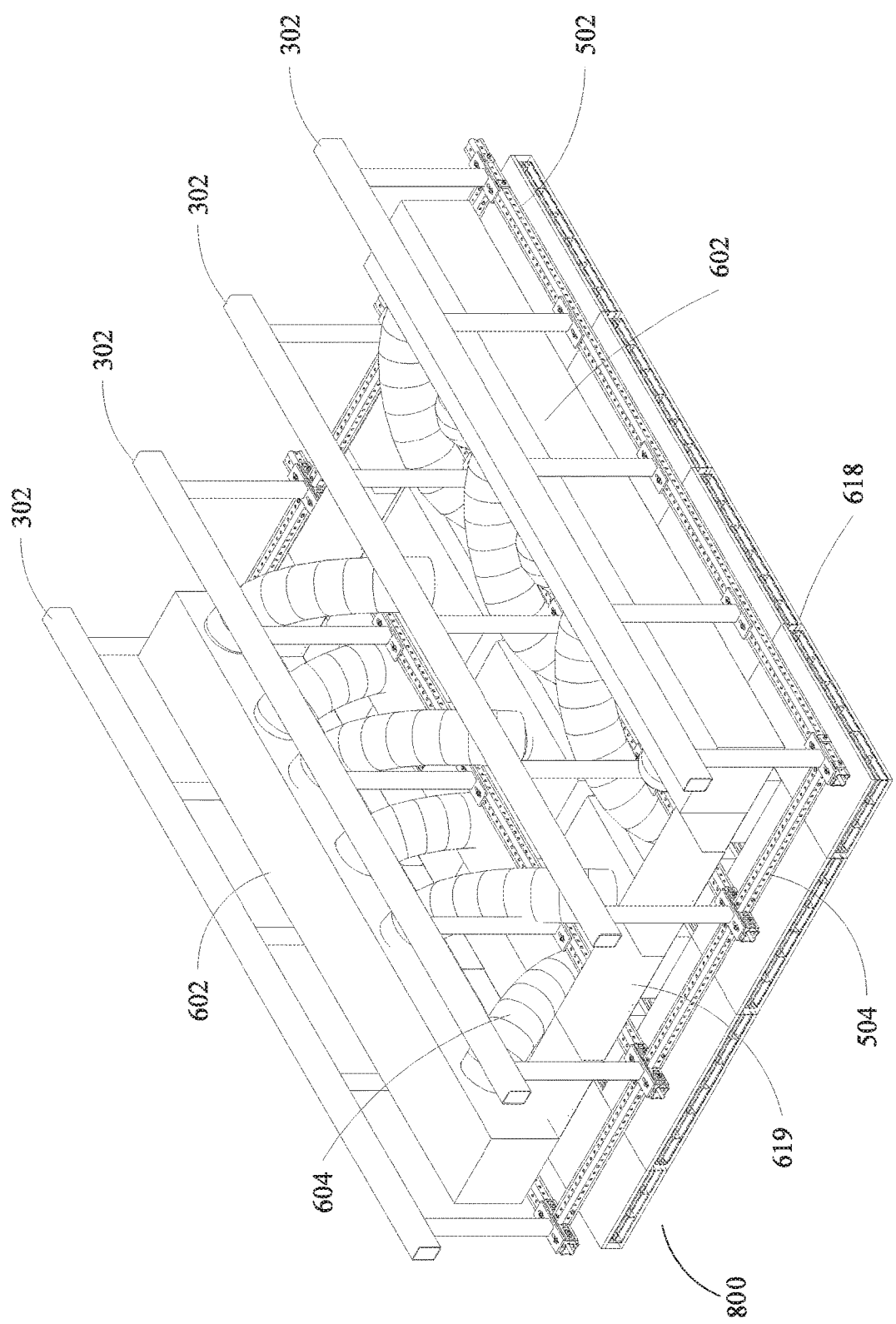
FIG. 9 depicts an isometric view of an assembled operating room ceiling system according to an embodiment of the present disclosure.

FIG. 9 is a different view of the completed universal operating room ceiling system 800 according to an embodiment of the present invention. In FIG. 9, the frame and grid arrangement comprising red iron frames 302 and modular steel rails 502 serve as the platform for ceiling system 800. Attached directly above the grid formed from steel rails 502 is track assembly 606. Track assembly 606 will house and serve as an access point for connection of medical gas lines, as well as electrical and data cabling. Above track assembly 606 are a pair of HVAC trunk lines 602. These trunk lines 602 act as the interface to facility HVAC equipment that carries cooled and heated air to the operating space. By making trunk lines 602 a part of the pre-fabricated and universal operating room ceiling system 800, complex coordination involved in dealing with pre-installed HVAC ducts and equipment placed by a variety of vendors and sourced to a wide range of manufacturers is removed. Each trunk line 602 includes ports from which ducts 604 emanate. Ducts 604 end at diffuser panels 620 located within ceiling assembly 618. Ceiling assembly 618 is the ceiling portion of system 800 that is in direct contact with the operating room. That is, ceiling assembly 618 at least in part serves as the physical ceiling in the operating room.

Also located in ceiling assembly 618 are various lighting assemblies 620. The diffusers 620 and lighting assemblies 619 within ceiling assembly 618 may be arranged in various ways, most specifically to direct lighting to necessary areas according to the arrangement of a particular operating room. The modular nature of ceiling assembly 618 makes movement of diffusers and lighting panels relatively simple. Note that FIG. 9 also shows that ducts 604 reside within the perimeter of track assembly 606 in order to isolate duct work and reduce interference with initial installation or subsequent modification of operating room equipment or equipment location. The various components of operating room ceiling systems described herein can be readily configured for relocation of surgical equipment and/or to support additional equipment.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solution to problems that are described herein with regard to specific embodiments are not intended to be construed as a critical, required, or essential feature or element of any or all the claims.

What is claimed is:

1. An operating room ceiling system, comprising:
 a plurality of steel support frames;
 a ceiling assembly having at least one light assembly and at least one diffuser assembly;
 a first substantially hollow track assembly positioned fully above and distinct from the at least one light assembly and the at least one diffuser assembly in an interstitial space of an operating room for supporting medical equipment; and
 at least one ventilation line positioned above the first substantially hollow track assembly,
 wherein the first substantially hollow track assembly is configured to accept power cables, medical gas lines, and communication cables associated with positioned and re-positioned medical equipment,
 wherein the ceiling assembly is on a first horizontal plane and the first substantially hollow track assembly is on a second horizontal plane.

2. The operating room ceiling system of claim 1, further comprising a second substantially hollow track assembly.

3. The operating room ceiling system of claim 2, wherein the second substantially hollow track assembly is positioned above the ceiling assembly in the interstitial space of the operating room for supporting medical equipment.

4. The operating room ceiling system of claim 2, wherein the at least one ventilation line is horizontally positioned between the first substantially hollow track assembly and the second substantially hollow track assembly.

5. The operating room ceiling system of claim 1, wherein the first substantially hollow track assembly and the second substantially hollow track assembly are manufactured from plastic.

6. The operating room ceiling system of claim 1, wherein the first substantially hollow track assembly and the second substantially hollow track assembly are manufactured from metal.

7. The operating room ceiling system of claim 1, wherein the plurality of steel support frames comprises a horizontal member and a plurality of vertical members.

8. The operating room ceiling system of claim 7, further comprising a plurality of headed spikes mounted to at least one of the plurality of steel support frames for connecting the at least one steel support frame to a concrete beam.

9. The operating room ceiling system of claim 1, further comprising a modular steel track in communication with the plurality of steel support frames and the first substantially hollow track assembly.

10. A pre-fabricated grid located above an operating room ceiling, comprising:
 a ceiling assembly having at least one light assembly and at least one diffuser assembly;
 a first substantially hollow track assembly positioned fully above and distinct from the at least one light assembly and the at least one diffuser assembly in an interstitial space of an operating room for supporting medical equipment;
 at least one ventilation line positioned above the first substantially hollow track assembly; and
 a modular steel track configured in a grid pattern connected to the first substantially hollow track assembly;
 wherein the first substantially hollow track assembly is configured to accept power cables, medical gas lines, and communication cables associated with positioned and re-positioned medical equipment within the operating room,
 wherein the ceiling assembly is on a first horizontal plane and the first substantially hollow track assembly is on a second horizontal plane.

11. The pre-fabricated grid of claim 10, further comprising a second substantially hollow track assembly.

12. The pre-fabricated grid of claim 11, wherein the second substantially hollow track assembly is positioned above the ceiling assembly in the interstitial space of the operating room for supporting medical equipment.

13. The pre-fabricated grid of claim 11, wherein the at least one ventilation line is horizontally positioned between the first substantially hollow track assembly and the second substantially hollow track assembly.

14. The pre-fabricated grid of claim 11, further comprising a plurality of headed spikes mounted to at least one of the plurality of steel support frames for connecting the at least one steel support frame to a concrete beam.

15. The pre-fabricated grid of claim 10, wherein the first substantially hollow track assembly and the second substantially hollow track assembly are manufactured from plastic.

16. The pre-fabricated grid of claim 10, wherein the first substantially hollow track assembly and the second substantially hollow track assembly are manufactured from metal.

17. The pre-fabricated grid of claim 10, further comprising a plurality of steel support frames comprising a horizontal member and a plurality of vertical members.

18. The pre-fabricated grid of claim 17, wherein the modular steel track is connected to a vertical member of the at least one of the plurality of steel support frames.

* * * * *